United States Patent [19]

von Stetten et al.

[11] Patent Number: 4,711,906

[45] Date of Patent: Dec. 8, 1987

[54] LIQUID DICLOFENAC PREPARATIONS

[75] Inventors: Otto von Stetten, Schelklingen, Fed. Rep. of Germany; Pyare L. Seth, Aesch, Switzerland; Franz Schmid, Pfaffenhofen; Kurt Rauchle, Blaubeuren, both of Fed. Rep. of Germany

[73] Assignee: Merckle GmbH, Blaubeuren, Fed. Rep. of Germany

[21] Appl. No.: 811,424

[22] Filed: Dec. 20, 1985

[30] Foreign Application Priority Data

Dec. 21, 1984 [DE] Fed. Rep. of Germany ....... 3446873

[51] Int. Cl.$^4$ ...................... A61K 09/06; A61K 27/00
[52] U.S. Cl. ..................................... 514/561; 514/538; 514/886; 514/887
[58] Field of Search ................ 514/561, 538, 886, 887

[56] References Cited

U.S. PATENT DOCUMENTS

| 3,220,923 | 11/1965 | Scholtan | 514/538 |
| 3,652,762 | 3/1972 | Sallmann et al. | 424/60 |
| 4,427,670 | 1/1984 | Ofuchi et al. | 514/887 |
| 4,540,572 | 9/1985 | Seth | 514/887 |
| 4,593,046 | 6/1986 | Gruber | 514/886 |
| 4,594,357 | 6/1986 | Dell et al. | 514/561 |

FOREIGN PATENT DOCUMENTS 59-33211  2/1984  Japan .................................. 514/887

OTHER PUBLICATIONS

Fiedler, "Lexikon der Hilfsstoffe fur Pharmazie, Kosmetic und angrenzende Gebiete", pp. 726–731 and 761–764 (1981).

Primary Examiner—Ronald W. Griffin
Attorney, Agent, or Firm—Robbins & Laramie

[57] ABSTRACT

Disclosed are aqueous, stable, relatively concentrated solutions of diclofenac, which contain a mixture of propylene glycol and polyethylene glycol in defined quantitative proportions. The solutions preferably contain a local anesthetic such as lidocaine and a reducing agent as stabilizer.

19 Claims, No Drawings

LIQUID DICLOFENAC PREPARATIONS

The present invention relates to stable liquid diclofenac preparations which are particularly suited for parenteral active ingredient application. Diclofenac is the international trivial name of the active ingredient [2-(2,6-dichloro-anilino)-phenyl] acetic acid; it is a non-steroidal anti-rheumatic agent which is applied in the symptomatic therapy of rheumatism. Due to the relatively large "first-pass-effect" of the substance and for faster flooding it is desirable to use injection solutions, in which an amount of 75 mg should be used per injection. For intramuscular injections, however, the volume is to be kept as low as possible.

Due to the relatively bad solubility of diclofenac in water an aqueous injection solution with a reasonable volume cannot be obtained. Moreover, diclofenac is relative instable in solution. Therefore, the object of the present invention was to make available diclofenac preparations which can be injected and which, with a low injection volume, allow the relatively pain-free injection of therapeutically sufficient amounts of drugs and which, moreover, can be stored.

The U.S. Pat. No. 3,652,762 discloses aqueous, proplene-glycol-containing sun-tan lotions which contain about 1 weight percent diclofenac.

Presently available diclofenac injection solutions contain the desired application amount of 75 mg diclofenac sodium in 3 ml solution, that is, its active ingredient content amounts to 2.5%. Its pH value amounts to pH 8.5. Propylene glycol and mannite and/or sorbit and benzyl alcohol have been used as solubilizers and/or preservatives as well as sulfite as stabilizer. Additions of local anesthetics in therapeutically active amounts for the prevention of injection pain are not contained in the known preparations, and are not possible either for solubility reasons in the solvent systems used so far. It is not possible either to additionally include in the solution further drugs, for instance, steroids as additional anti-inflammatorily active substances, if the injection volume is to be kept within reasonable limits.

Propylene glycol and polyethylene glycol have been known as solubilizers. Therefore, first of all attempts were made to dissolve diclofenac in a mixture of water and propylene glycol, however, such a system did not demonstrate sufficient dissolving properties. When using polyethylene glycol instead of propylene glycol a higher degree of dissolution was reached, however, the solution was too viscous in order to be used for parenteral application.

It has now surprisingly been found that comparatively highly-concentrated active ingredient solutions, at least at higher pH values, can be obtained with a solvent system consisting of water and a mixture of propylene glycol and polyethylene glycol in the amount ratios given below.

Furthermore, it has surprisingly been found that an even better dissolution of the diclofenac can be obtained when a local anesthetic, i.e. lidocaine, is added. Due to this a sufficient degree of solubility is obtained already at lower pH values, values which correspond more to the physiological value.

Just like the lidocaine most of the local anesthetics are slightly basic substances forming salts with acids such as HCl. The local anesthetics are expediently used in the form of their acid addition salts, especially as hydrochlorides. Local anesthetics of the the kind of lidocaine are, in particular, bupivacaine, etidocaine, pyrrocaine and mepivacaine.

The effect of the lidocaine is surprising especially since it was found that the solvent system is more effective at a higher pH value than at a lower pH value and the addition of lidocaine-HCl certainly does not increase the pH value, but decreases it.

Furthermore, it has been found that the addition of lidocaine does not only improve the degree of solubility, that is, the physical stability but also the chemical stability of the solutions when at the same time a reducing agent is added.

According to the invention it is possible to hold the desired application amount of 75 mg in stable solution in as little as 2 ml injection solution.

Thus, the subject matter of the invention is liquid diclofenac preparations, in particular, for the parenteral application, consisting of a solution of diclofenac or one of its salts and, if desired, further pharmaceutical active ingredients and auxiliary substances in a solvent, the solvent consisting of 10-70 weight % preferably 20-50 weight %, of a mixture of (a) propylene glycol and (b) polyethylene glycol and 90-30 weight %, preferable 80-50 weight % of water, and in the solvent mixture the weight ratio of proylene glycol:polyethylene glycol being between 9.5:0.5 and 0.5:9.5, preferably between 3:1 and 1:3, especially preferably between 2:1 and 1:2.

In general the preparations contain 1.5 to 6 weight percent diclofenac, preferably 3 to 4 weight % diclofenac sodium.

Polyethylene glycol 400 is preferably used as polyethylene glycol.

The concentration of an added local anesthetic, especially lidocaine, may fluctuate between 0.1 weight % and 5 weight %, and is preferably in the range of 0.5 weight % to 2 weight %, in terms of lidocaine-HCl. The addition of a local anesthetic is not undesired also for medical reasons, for the prevention of the injection pain.

In the preparations according to the invention it is possible to adjust the pH value in the range between pH=6.5 and pH=8.

For the purpose of chemical stabilization a reducing agent is added as stabilizer to the solutions as well. In this connection, endogenous substances such as cysteine or thiosulfate are to be preferred. In the case of usual solvents a precipitation which cannot be clearly defined frequently occurs when using cysteine. In the preparations according to the invention such a precipitation does not occur, not even after months of storage. When using N-acetyl-cysteine, a pharmaceutically acceptable active ingredient when used in higher concentrations, the possibility of precipitations is even further reduced. In the preparations according to the invention the stabilizers added can be sulfite, cysteine and/or cysteine-hydrochloride, acetyl-cysteine and/or -hydrochloride, thiosulfate etc., preferably sulfite, cysteine, acetylcyteine, especially preferably sulfite and acetyl-cysteine, in concentrations between 0.05 weight % and 5 weight %, preferably between 0.05 weight and 3 weight %.

In the therapy of rheumatism it is frequently necessary to use, for the purpose of enhancing the effect, in addition to diclofenac also other anti-inflammatory substances, preferably steroids, for instance, glucocorticoids such as dexamethasone or prednisolone. In commonly used solvents steroids or suitable derivatives beside diclofenac are relatively poorly soluble. In the preparations according to the invention, however, it is possible to dissolve, in a storage-stable manner, in addition to 75 mg diclofenac sodium also larger amounts of steroid, for instance, 25 mg prednisolone in the form of 33 mg prednisolone-21-phosphate-disodium salt, in volumes which are preferred for intramuscular injections, for instance, 2 ml.

All percent indications relate to the complete injection solution.

COMPARATIVE TEST

Attempts have been made to bring in a stable solution 3.75 weight % diclofenac sodium, 0.1 weight % sodium disulfite and 0.01 weight % ehtylene-diamino-tetra acetic acid (EDTA) without the addition of lidocaine as well as by adding 1 weight % lidocaine in solvent systems of (a) 42 weight % polyethylene glycol (PEG), remainder water; (b) 42 weight % propylene glycol (PG), remainder water; (c) 24 weight % polyethylene glycol (PEG), 18 weight % propylene glycol (PG), remainder water, at pH 7 and/or pH 8. The percent indications relate to the entire mixture. Polyethylene glycol 400 was added as polyethylene glycol (PEG). The pH value was adjusted with soda lye. The ampoules were subjected to an alternating exposure of 6 hours room temperature −6 hours refrigerator during a period of 14 days. The results are listed in the table below. + marks that a stable solution was obtained, − marks that a stable solution was not obtained.

|  | 0% Lidocaine | | | 1% Lidocaine | | |
|---|---|---|---|---|---|---|
|  | 42% PEG | 42% PG | 24% PEG 18% PG | 42% PEG | 42% PG | 24% PEG 18% PG |
| pH 7 | (+) −* | − | − | + | − | + |
| pH 8 | + | − | + | + | − | + |

*Crystallization was found in a further check after 14 days.

The preparations with 42 % PEG were too viscous to be used for parenteral application.

EXAMPLE 1

7.5 diclofenac-Na is dissolved in a solution consisting of 48 g propylene glycol and 36 g polyethylene glycol 400. 20 mg EDTA, 200 mg Na-disulfite and 2 g lidocaine are added. After topping up with water to 195 ml a pH value of 8 is adjusted with soda lye and topped up to 200 ml. The solution is filled into ampoules of 2 each and sterilized at 120° C. for 20 minutes. The solution in the ampoules has been stored at room temperature for 3 years and is stable.

EXAMPLE 2

Analogously to Example 1 a diclofenac-Na solution was prepared, however, instead of 200 mg Na-disulfite 200 mg acetyl-cysteine-HCl were added. After 3 weeks of storage at 81° C. the content of diclofenac-Na decreased only negligibly. A precalculation by W. Grimm's method showed a keeping quality of more than 3 years.

EXAMPLE 3

Analogously to Example 1 a diclofenac-Na solution was produced, however, instead of 200 mg Na-disulfite 200 mg cysteine-HCl were added. After 3 weeks of storage at 81° C. the content of diclofenac-Na decreased only negligibly. A precalculation by W. Grimm's method showed a keeping quality of more than 3 years.

EXAMPLE 4

A solution in accordance with Example 2 was produced, however, an additional 3.3 g prednisolone-21-phosphate-di-sodium salt was added. The solution was filled into ampoules of 2 ml each and sterilized at 100° C. for 30 minutes. A stress test with storage at 81° C. allows one to expect a keeping quality of more than 3 years.

EXAMPLE 5

A solution analogously to Example 2 was produced. An additional 524 mg dexamthasore-21-phosphate-di-sodium salt was added. The solution was filled into ampoules of 2 ml each and sterilized at 100 ° C. for 30 minutes. A stress test with storage at 81° C. allows one to expect a keeping quality of more than 3 years.

We claim:

1. A stable, liquid diclofenac preparation, especially for the parenteral application, consisting of a solution of diclofenac or one of its salts in an amount of 1.5–6.0 weight % diclofenac in a solvent, wherein the solvent consists of 10–70 weight % of a mixture of (a) propylene glycol and (b) polyethylene glycol and 30–90 weight % water, and the weight ratio of (a) propylene glycol to (b) polyethyelene glycol is between 9.5:0.5 and 0.5:9.5.

2. The diclofenac preparation according to claim 1, wherein the weight ratio of (a) propylene glycol to (b) polyethylene glycol is between 2:1 and 1:2.

3. The dicyclofenac preparation according to claim 1 having a pH value of 5.5–9.

4. The diclofenac preparation according to claim 1 containing a polyethylene glycol 400 as the polyethylene glycol component.

5. The diclofenac prparations according to claim 1 which further consists of 0.1–5 weight % of a local anesthetic.

6. The diclofenac preparation according to claim 5, wherein the local anesthetic is lidocaine.

7. The diclofenac preparation according to claim 6 having a pH value of 7.5–8.

8. The diclofenac preparation according to claim 1 which further consists of 0.05 to 5 weight % of a reducing agent as stabilizer.

9. The diclofenac preparation according to claim 8, wherein the reducing agent is selected from the group consisting of sodium-disulfite, cysteine-hydrochloride, N-acetyl cysteine hydrochloride, sodium-thiosulfate and mixtures thereof.

10. The diclofenac preparation according to claim 1 which further consists of an anti-inflammatorily active drug.

11. The diclofenac preparation according to claim 9, wherein said preparation consists essentially of 3 to 4 weight % diclofenac sodium, about 24 weight % propylene glycol, about 18 weight % polyethylene glycol 400, about 1 weight % lidocaine-hydrochloride, about 0.1 weight % sodium-disulfite, and the remainer being water, having a pH value of 8.

12. The diclofenac preparation according to claim 1 wherein said solvent consists of 20–50 weight % of a mixture of (a) propylene glycol and (b) polyethylene glycol and 50–80 weight % of water.

13. The diclofenac preparation according to claim 1 wherein the weight ratio of (a) glycol to (b) polyethylene glycol is between 3:1 and 1:3.

14. The diclogenac preparation according to claim 3 having a pH of 6.0–8.5.

15. The diclofenac preparation according to claim 3 having a pH of 6.5–8.0.

16. The diclofenac preparation of claim 5 wherein 0.5–2 weight % of a local anesthetic is present.

17. A liquid diclofenac preparation, especially for the parental application, consisting of a solution of diclofenac or one of its salts in a solvent, wherein the solvent consists of 20–50 weight % of a mixture of propylene glycol and polyethylene glycol in a weight ratio of 3:1–1:3 and 50–80 weight % of water.

18. A stable, liquid diclofenac preparation, especially for the parenteral application, consisting of a solution of diclofenac or one of its salts in an amount of 1.5–6.0 weight % diclofenac, 0.5–2 weight % of a local anesthetic, 0.05–5 weight % of a reducing agent in a solvent, wherein the solvent consists of 20–50 weight % of a mixture or propylene glycol and polyethylene glycol in a weight ratio of 3:1–1:3 and 50–80 weight % of water.

19. The diclofenac preparation of claim 18 wherein the local anesthetic is lidocaine and the reducing agent is sodium disulfite.

* * * * *